(12) United States Patent
Adkerson (10) Patent No.: US 10,352,578 B2
(45) Date of Patent: Jul. 16, 2019

(54) ADAPTIVE OPTIMIZATION FOR DYNAMIC ROOM PRESSURIZATION CONTROL

(71) Applicant: BOARD OF REGENTS, THE UNIVERSITY OF TEXAS SYSTEM, Austin, TX (US)

(72) Inventor: Curtis D. Adkerson, Pearland, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 245 days.

(21) Appl. No.: 15/615,383

(22) Filed: Jun. 6, 2017

(65) Prior Publication Data

US 2017/0356666 A1 Dec. 14, 2017

Related U.S. Application Data (60) Provisional application No. 62/347,983, filed on Jun. 9, 2016.

(51) Int. Cl.
| | |
|---|---|
| *F24F 11/64* | (2018.01) |
| *F24F 11/00* | (2018.01) |
| *G05D 16/20* | (2006.01) |
| *G01N 1/26* | (2006.01) |
| *F24F 11/30* | (2018.01) |

(Continued)

(52) U.S. Cl.
CPC .......... *F24F 11/0001* (2013.01); *F24F 11/30* (2018.01); *F24F 11/64* (2018.01); *F24F 11/65* (2018.01); *G01N 1/26* (2013.01); *G05D 16/028* (2019.01); *G05D 16/2073* (2013.01); *F24F 2110/50* (2018.01)

(58) Field of Classification Search
CPC .................................. F24F 11/64; F24F 11/00
USPC ......................................................... 454/255
See application file for complete search history.

(56) References Cited

U.S. PATENT DOCUMENTS

| | | |
|---|---|---|
| 5,538,471 A | 7/1996 | Guiles, Jr. |
| 6,033,302 A | 3/2000 | Ahmed et al. |

(Continued)

OTHER PUBLICATIONS

Siemens Industry; Document No. 149-977; Volumetric Airflow Tracking vs. Differential Pressure Sensing; Room Pressurization Control Methods; Feb. 2003.

*Primary Examiner* — Steven B McAllister
*Assistant Examiner* — Samantha A Probst
(74) *Attorney, Agent, or Firm* — Daniel J. Chalker; Chalker Flores, LLP (57) ABSTRACT

An apparatus and method controls an environmental control system to maintain a differential pressure between a room and one or more adjacent areas by (1) determining a differential pressure error based on the differential pressure and a differential pressure set point using a proportional-integral-derivative (PID) controller; (2) increasing an air change per hour set point whenever one or more first parameters are satisfied; (3) decreasing the air change per hour set point whenever one or more second parameters are satisfied; and (4) sending one or more control signals to the environmental control system that maintain the differential pressure between the room and the one or more adjacent areas by adjusting: (a) the leading airflow to be approximately equal to the air flow change set point multiplied by a volume of the room divided by 60, and (b) the tracking airflow to maintain a volume differential set point.

20 Claims, 5 Drawing Sheets

(51) Int. Cl.
  *F24F 11/65* (2018.01)
  *G05D 16/00* (2006.01)
  *F24F 110/50* (2018.01)

(56) References Cited

U.S. PATENT DOCUMENTS

| | | | | |
|---|---|---|---|---|
| 6,081,750 | A * | 6/2000 | Hoffberg | G06F 3/00 700/17 |
| 6,400,996 | B1 * | 6/2002 | Hoffberg | G05B 19/0426 370/218 |
| 7,006,881 | B1 * | 2/2006 | Hoffberg | G05B 15/02 700/17 |
| 7,813,822 | B1 * | 10/2010 | Hoffberg | G06K 9/00369 381/73.1 |
| 8,082,946 | B2 * | 12/2011 | Laverdiere | G05D 16/2013 137/487.5 |
| 8,364,136 | B2 * | 1/2013 | Hoffberg | G05B 15/02 340/426.15 |
| 8,580,569 | B2 * | 11/2013 | Linder | B01L 3/5027 436/55 |
| 2006/0111816 | A1 * | 5/2006 | Spalink | G05D 23/1931 700/276 |
| 2006/0200259 | A1 * | 9/2006 | Hoffberg | G05B 15/02 700/86 |
| 2006/0259195 | A1 * | 11/2006 | Eliuk | A61J 1/20 700/245 |
| 2007/0061022 | A1 * | 3/2007 | Hoffberg-Borghesani | G05B 19/0426 700/83 |
| 2007/0082601 | A1 | 4/2007 | Desrochers et al. | |
| 2012/0046792 | A1 * | 2/2012 | Secor | F24F 11/30 700/276 |
| 2012/0303164 | A1 * | 11/2012 | Smith | H05K 7/20745 700/276 |
| 2012/0323374 | A1 * | 12/2012 | Dean-Hendricks | G05B 15/00 700/276 |
| 2013/0030555 | A1 * | 1/2013 | Starr | G05B 23/0216 700/83 |
| 2013/0158720 | A1 * | 6/2013 | Zywicki | G05D 23/1934 700/276 |
| 2013/0190899 | A1 * | 7/2013 | Slessman | G05B 13/02 700/28 |
| 2013/0201316 | A1 * | 8/2013 | Binder | H04L 67/12 348/77 |
| 2014/0200718 | A1 * | 7/2014 | Tessier | G05D 23/1902 700/276 |
| 2014/0214212 | A1 * | 7/2014 | Leen | G05D 23/1902 700/276 |
| 2015/0120015 | A1 * | 4/2015 | Fadell | G08B 19/005 700/90 |
| 2015/0134123 | A1 * | 5/2015 | Obinelo | G05B 15/02 700/277 |
| 2015/0148965 | A1 * | 5/2015 | Lemire | G05B 15/02 700/276 |
| 2015/0156031 | A1 * | 6/2015 | Fadell | H04L 12/2816 700/276 |
| 2015/0159903 | A1 * | 6/2015 | Marak | G05B 15/02 700/278 |
| 2015/0297778 | A1 * | 10/2015 | Conroy | G06Q 10/08 239/11 |

* cited by examiner

ADAPTIVE OPTIMIZATION FOR DYNAMIC ROOM PRESSURIZATION CONTROL

CROSS-REFERENCE TO RELATED APPLICATIONS

This non-provisional Patent Application claims priority to U.S. Provisional Patent Application Ser. No. 62/347,983, filed Jun. 9, 2016, entitled "Adaptive Optimization for Dynamic Room Pressurization Control," the contents of which is incorporated by reference herein in its entirety.

INCORPORATION-BY-REFERENCE OF MATERIALS FILED ON COMPACT DISC

None.

TECHNICAL FIELD OF THE INVENTION

The present invention relates generally to the field of environmental control systems and, more particularly, to adaptively optimizing dynamic room pressurization control.

STATEMENT OF FEDERALLY FUNDED RESEARCH

None.

BACKGROUND OF THE INVENTION

Room pressurization is important for preventing unwanted airflow in certain environments, such as negative static pressure in chemical and biological facilities, or positive static pressure in food and drug processing operations. A room can be maintained at a negative static pressure with respect to an adjacent area by airflow tracking, which always removes more air from the room than is supplied to the room. This creates a slight vacuum condition within the room. Similarly, a room can be maintained at a positive static pressure with respect to an adjacent area by airflow leading, which always supplies more air to the room than is removed from the room. This creates a slight pressurized condition within the room.

Pressure dependent environments that use 100% outside air supply typically consume a substantial amount of energy to operate because outside air is so expensive to condition. Part of the problem lies with limitations in the terminal box controller configuration. When static values, such as a differential pressure set point and air change per hour set point, are used for terminal box controller configuration, the room will typically have high energy usage, compliance related issues, or both when there is an event or unfavorable change in the heating, ventilating and air conditioning (HVAC) system.

As a result, there is a need for room pressurization control systems and methods that adaptively optimize the air change per hour set point to maximize energy savings while operating within the environmental requirements of the room.

SUMMARY OF THE INVENTION

Various embodiments of the present invention provide room control systems and methods that adaptively optimize the air change per hour set point to maximize energy savings while operating within the environmental requirements of the room, such as maintaining a differential pressure between a room and one or more adjacent areas. For example, the present invention controls an environmental control system to maintain a differential pressure between a room and one or more adjacent areas by (1) determining a differential pressure error based on the differential pressure and a differential pressure set point using a proportional-integral-derivative (PID) controller; (2) increasing an air change per hour set point whenever one or more first parameters are satisfied; (3) decreasing the air change per hour set point whenever one or more second parameters are satisfied; and (4) sending one or more control signals to the environmental control system that maintain the differential pressure between the room and the one or more adjacent areas by adjusting: (a) the leading airflow to be approximately equal to the air flow change set point multiplied by a volume of the room divided by 60, and (b) the tracking airflow to maintain a volume differential set point.

One embodiment of the present invention provides a method for controlling an environmental control system to maintain a differential pressure between a room and one or more adjacent areas by: (1) monitoring a temperature in the room, the differential pressure, a leading airflow for the room and a tracking airflow for the room; (2) determining a differential pressure error based on the differential pressure and a differential pressure set point using a proportional-integral-derivative (PID) controller; (3) increasing an air change per hour set point whenever: (a) the temperature exceeds a high temperature threshold, (b) the temperature falls below a low temperature threshold and the environmental control system is operating at approximately 100% of heating capacity, or (c) the differential pressure error is greater than a first percentage of a maximum delta between the leading airflow and the tracking airflow; (4) decreasing the air change per hour set point whenever the differential pressure error is less than a second percentage of the maximum delta between the leading airflow and the tracking airflow, and the temperature is above the low temperature threshold and below the high temperature threshold; and (5) sending one or more control signals to the environmental control system that maintain the differential pressure between the room and the one or more adjacent areas by adjusting: (a) the leading airflow to be approximately equal to the air flow change set point multiplied by a volume of the room divided by 60, and (b) the tracking airflow to maintain a volume differential set point.

Another embodiment of the present invention provides an apparatus for controlling an environmental control system to maintain a differential pressure between a room and one or more adjacent area that includes a communications interface, a memory, and a processor communicably coupled to the communications interface and the memory. The processor (1) receives a temperature in the room, the differential pressure, a leading airflow for the room and a tracking airflow for the room via the communications interface, (2) determines a differential pressure error based on the differential pressure and a differential pressure set point using a proportional-integral-derivative (PID) algorithm, (3) increases an air change per hour set point whenever: (a) the temperature exceeds a high temperature threshold, (b) the temperature falls below a low temperature threshold and the environmental control system is operating at approximately 100% of heating capacity, or (c) the differential pressure error is greater than a first percentage of a maximum delta between the leading airflow and the tracking airflow, (4) decreases the air change per hour set point whenever the differential pressure error is less than a second percentage of the maximum delta between the leading airflow and the tracking airflow, and the temperature is above the low temperature threshold and below the high temperature threshold, and (5) sends one or more control signals to the environmental control system via the communications interface that maintain the differential pressure between the room and the one or more adjacent areas by adjusting: (a) the leading airflow to be approximately equal to the air flow change set point multiplied by a volume of the room divided by 60, and (b) the tracking airflow to maintain a volume differential set point.

The present invention is described in detail below with reference to the accompanying drawings.

BRIEF DESCRIPTION OF THE DRAWINGS

The above and further advantages of the invention may be better understood by referring to the following description in conjunction with the accompanying drawings, in which.

DETAILED DESCRIPTION OF THE INVENTION

The current invention now will be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art.

Adaptive Optimization for Dynamic Room Pressurization Control (AODRPC) is an innovative way to lower the outside air consumption of pressure dependent environments and adapt to adverse changes in the HVAC system automatically while maintaining space requirements. With AODRPC, the room will not only react accordingly to system malfunctions such as a pressure change in an adjacent space or the air distribution system, but will do it using the lowest possible air change rates for the application.

Some benefits of AODRPC may include: (1) dynamic room pressurization control; (2) the air change set point is dynamic and is reset based on demand allowing the room to operate at lowest air change rate possible saving the maximum amount of energy while operating within compliance of room requirements; (3) fast response to adverse changes in the HVAC system and/or pressure relationship between adjacent space(s); (4) automatic balance between all adjoining spaces that are using AODRPC; (5) does not require additional hardware in most cases; and/or (6) can be implemented as retro-commissioning.

Various embodiments of the present invention provide room control systems and methods that adaptively optimize the air change per hour set point to maximize energy savings while operating within the environmental requirements of the room, such as maintaining a differential pressure between a room and one or more adjacent areas. For example, the present invention controls an environmental control system to maintain a differential pressure between a room and one or more adjacent areas by (1) determining a differential pressure error based on the differential pressure and a differential pressure set point using a proportional-integral-derivative (PID) controller; (2) increasing an air change per hour set point whenever one or more first parameters are satisfied; (3) decreasing the air change per hour set point whenever one or more second parameters are satisfied; and (4) sending one or more control signals to the environmental control system that maintain the differential pressure between the room and the one or more adjacent areas by adjusting: (a) the leading airflow to be approximately equal to the air flow change set point multiplied by a volume of the room divided by 60, and (b) the tracking airflow to maintain a volume differential set point.

More specifically, AODRPC uses an offset between the leading airflow CFM and the tracking airflow CFM that is modulated to maintain differential pressure between adjacent space(s) at a desired set point. In one example, AODRPC will maintain between 93% and 97% (adjustable) of the maximum delta between supply and exhaust, conserving otherwise wasted energy.

Figure 1:
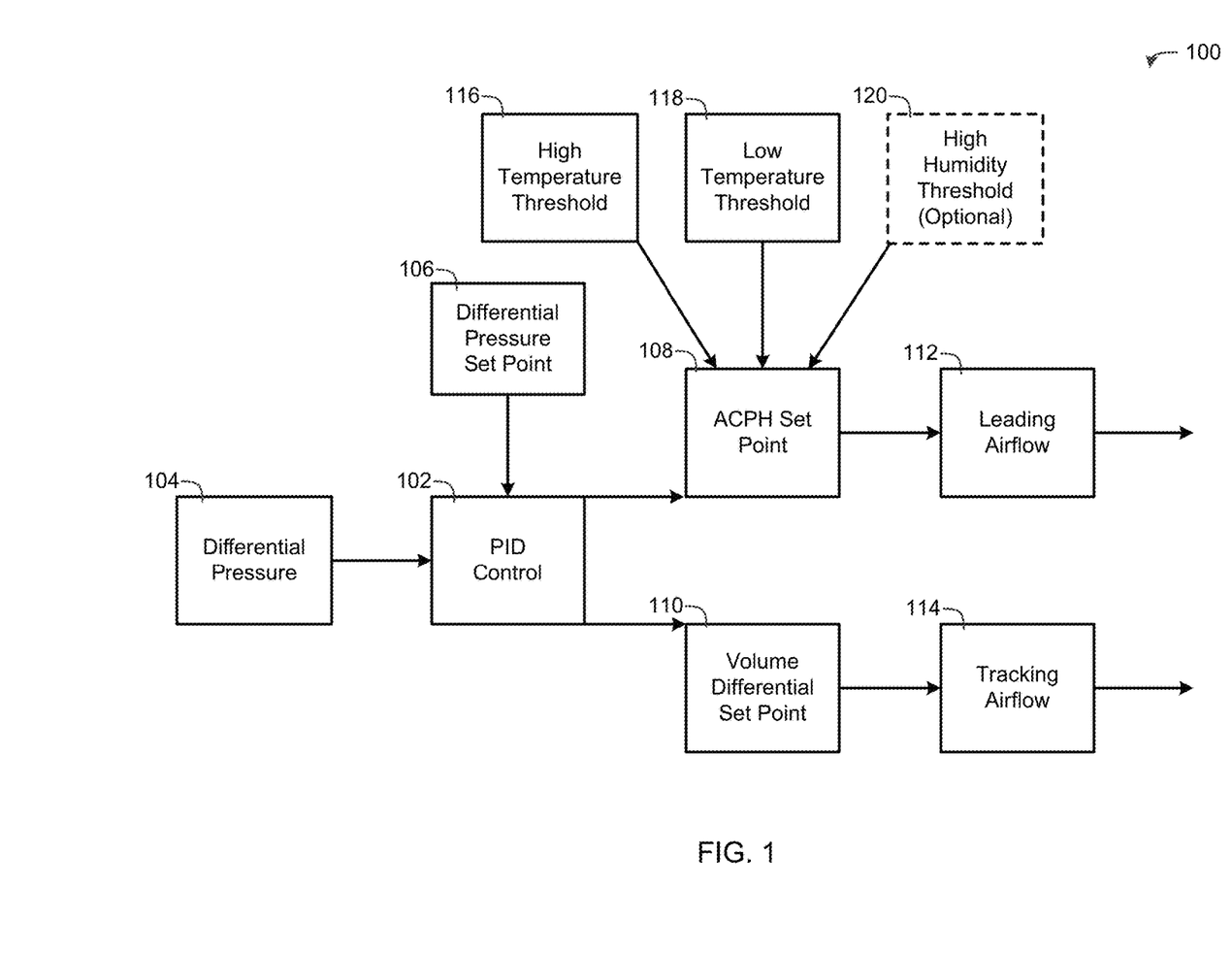
FIG. 1 is a flow chart of a method for adaptively optimizing a differential pressure between a room and one or more adjacent spaces according to an embodiment of the current invention.

Now referring to FIG. 1, a flow chart of a method 100 for adaptively optimizing a differential pressure between a room and one or more adjacent spaces according to an embodiment of the current invention is shown. A proportional-integral-derivative (PID) controller 102 receives a differential pressure 104, which is the difference in pressure measured between the pressure dependent room and adjacent space. The PID controller 102 continuously calculates an error value as the difference between a measured process variable (differential pressure 104) and a desired set point (differential pressure set point 106). The PID controller 102 attempts to minimize the error over time by adjustment of one or more control variables to a new value determined by a weighted sum. The PID controller 102 accounts for present values of the error (e.g., if the error is large and positive, the control variable will be large and negative), past values of the error (e.g., if the output is not sufficient to reduce the size of the error, the control variable will accumulate over time, causing the controller to apply a stronger action), and possible future values of the error, based on its current rate of change. The PID controller 102 deals with specific process requirements by tuning the three parameters of the model. The ACPH set point 108 is changed by the PID loop position to maintain an optimum volume differential set point 110, which maintains a volume differential between the leading airflow 112 (total supply) and tracking airflow 114 (total exhaust) of the room.

AODRPC uses an air change per hour (ACPH) set point 108 range (see e.g., FIG. 2) that is defined by the requirements of the room and will maintain the lowest air change rate possible to meet those requirements. It will automatically adjust the ACPH set point 108 based on the demand. In one example, if the delta between the leading airflow 112 and tracking airflow 114 exceeds 97% (adjustable), a high temperature threshold 116 has been met, a low temperature threshold 118 has been met and reheat is at maximum capacity, or a high humidity threshold 120 has been met (optional), the air change per hour set point 108 will be increased. The ACPH set point 108 will be decreased by the delta falling below 93% (adjustable) in accordance with the temperature and humidity being below their high thresholds 116 and 120 and the temperature being above the low threshold 118. All thresholds, and min/max air change set points will be determined by the requirements of the space. The humidity sequence is optional based on space requirements. The leading airflow 112 (LCFM) is determined by the pressure orientation of the room and is set by the ACPH set point 108 by $$LCFM=(ACPH \text{ Set Point} \times \text{Room Volume})/60.$$

Figure 2:
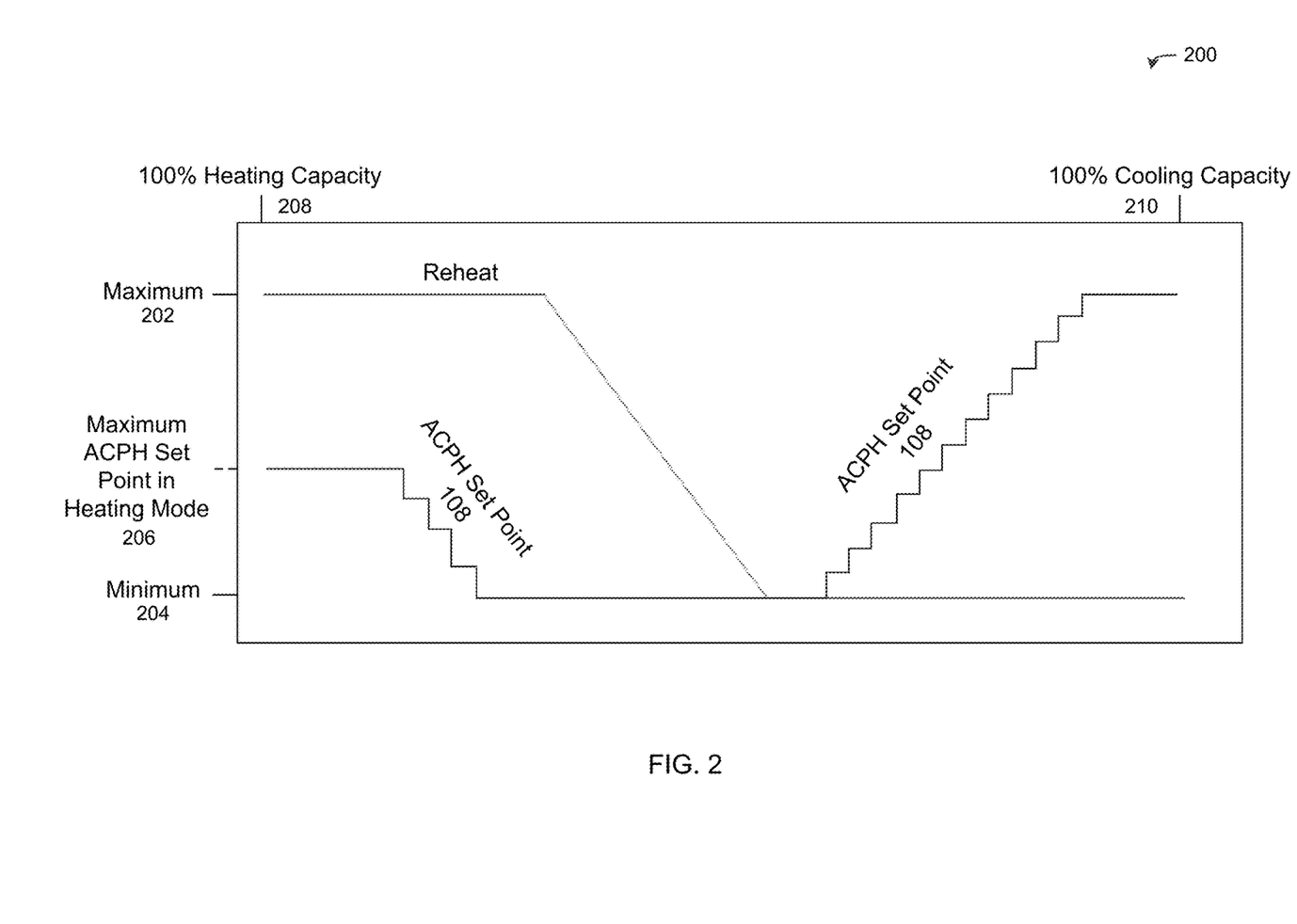
FIG. 2 is a graph showing an example of changing the air change per hour set point based on temperature according to an embodiment of the current invention.

The tracking airflow 114 is modulated to maintain the differential pressure 104 at the differential pressure set point 106. It will modulate from minimum and maximum set by the program, such as a minimum approximately equal to the leading airflow 112 and a maximum approximately equal to a minimum stable air terminal position as suggested by the manufacturer.

Figure 3:
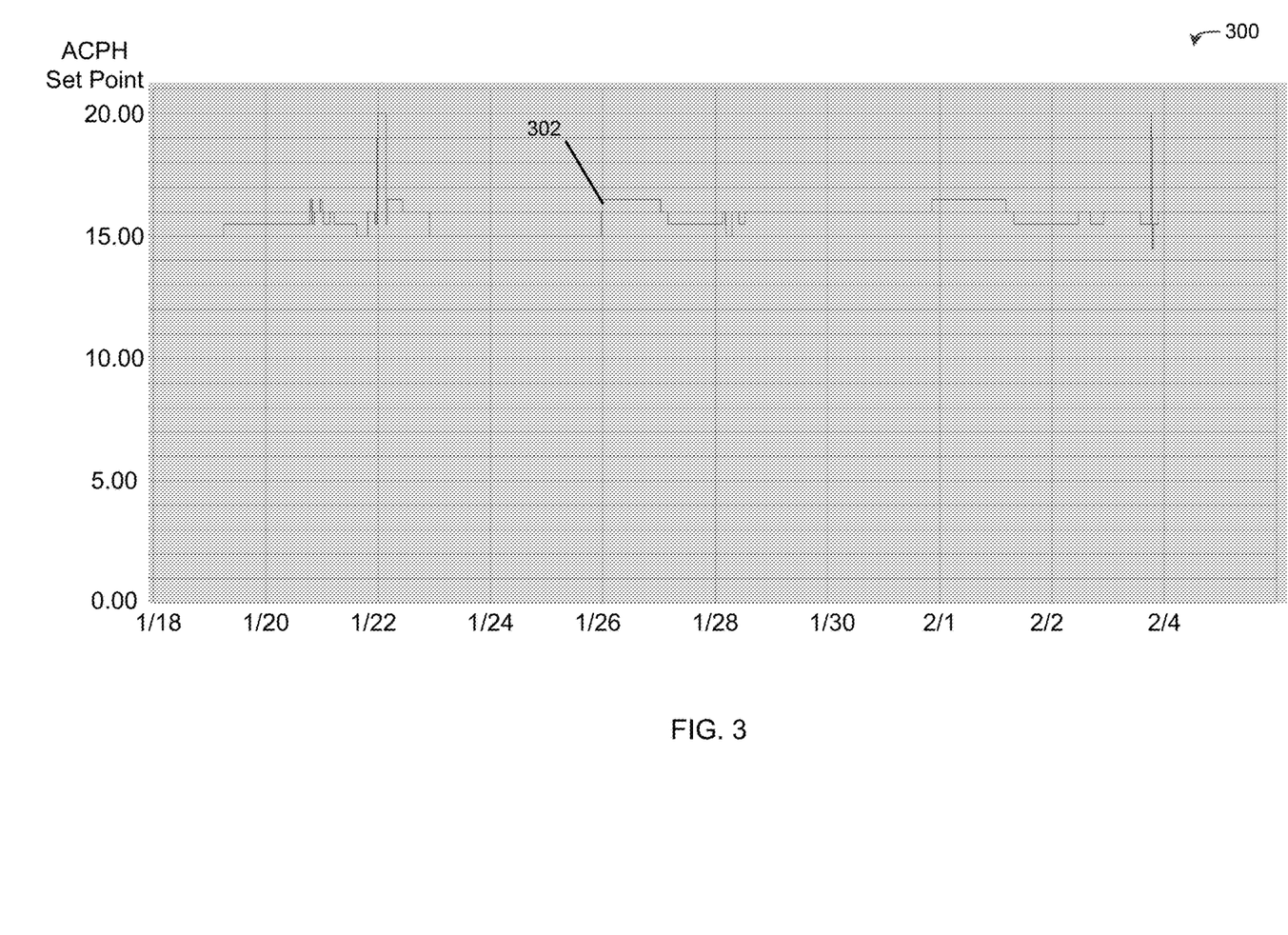
FIG. 3 is a graph showing a fifteen day trend of the air change per hour set point in a 225 square foot room according to an embodiment of the current invention.

Referring now to FIG. 2, a graph showing an example of changing the ACPH set point 108 based on temperature according to an embodiment of the current invention is shown. The ACPH set point 108 can have a maximum value 202 and a minimum value 204. The maximum value 202 can be based on other criteria, such as a first maximum value 206 when the environmental control system is operating at approximately 100% heating mode 208 and a second maximum value 202 when the environmental control system is operating at approximately 100% cooling mode 210. In another example, FIG. 3 shows a fifteen day trend of the ACPH set point 108 in a 225 square foot room according to an embodiment of the current invention.

Figure 4:
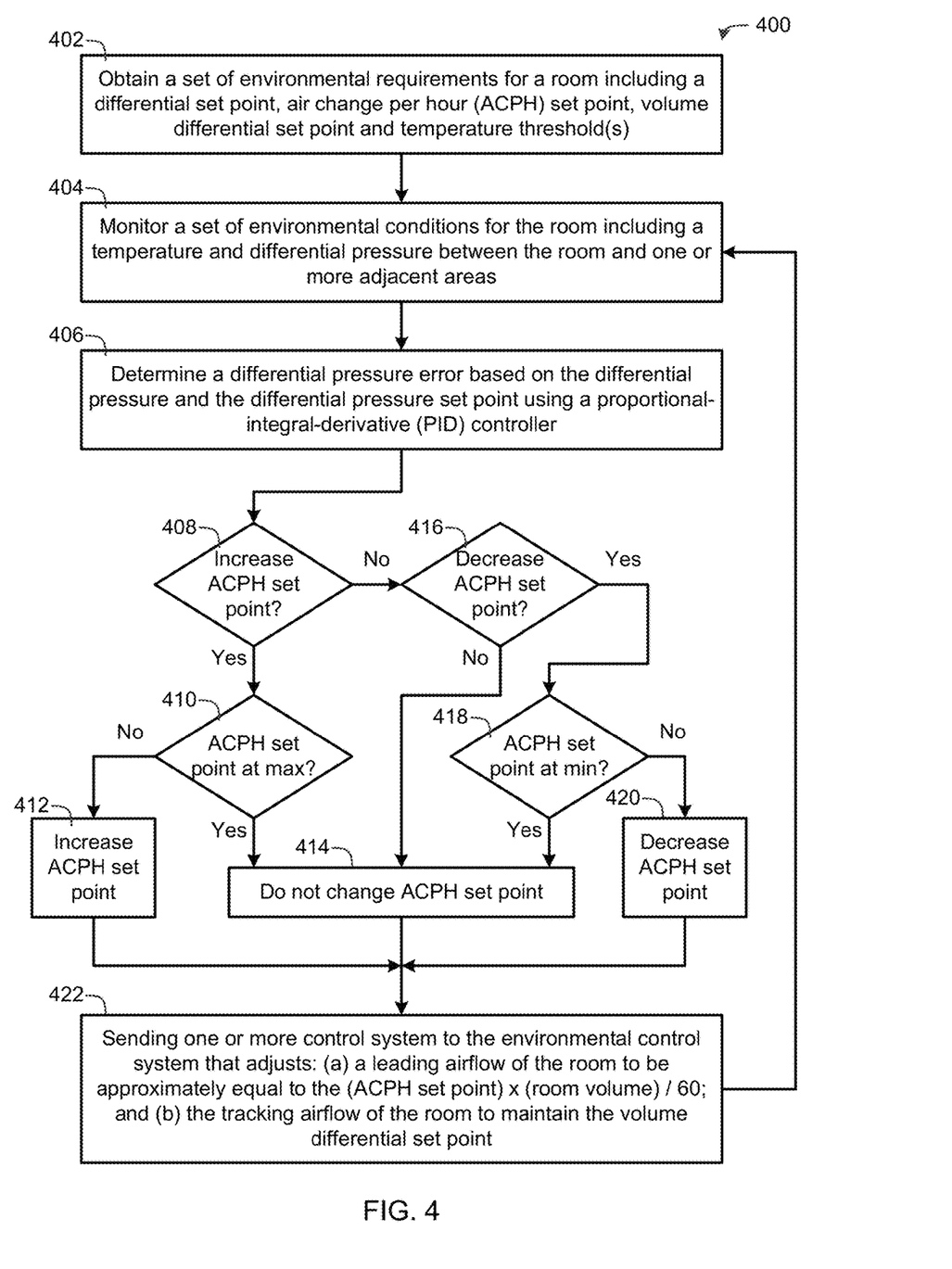
FIG. 4 is a flow chart of a method for controlling an environmental control system to maintain a differential pressure between a room and one or more adjacent areas according to an embodiment of the current invention.

Now referring to FIG. 4, a flow chart of a method 400 for controlling an environmental control system to maintain a differential pressure 104 between a room and one or more adjacent areas according to an embodiment of the current invention is shown. A set of environmental requirements for a room or operational parameters are obtained in block 402, which may include a volume of the room, high and/or low temperature threshold, high and/or low humidity threshold, differential pressure set point, ACPH set point (may also include one or more minimum or maximum values), volume differential set point, maximum delta between the leading airflow and the tracking airflow, and/or other desired operational parameters. Note that any of the environmental requirements can be changed automatically or manually while the method is being performed. A set of environmental conditions for the room are monitored in block 404, which may include a temperature and/or humidity in the room, differential pressure, leading airflow for the room, tracking airflow for the room, heating or cooling mode, and/or other desired current parameters (measured or calculated). A differential pressure error is determined using the PID controller based on the differential pressure and a differential pressure set point in block 406. The differential pressure error, set of environmental requirements and set of environmental conditions are evaluated to determine whether to increase the ACPH set point, decrease the ACPH set point, or leave the ACPH set point unchanged.

In one embodiment, the ACPH set point is increased whenever: (a) the temperature exceeds a high temperature threshold, (b) the temperature falls below a low temperature threshold and the environmental control system is operating at approximately 100% of heating capacity, or (c) the differential pressure error is greater than a first percentage (e.g., 97%) of a maximum delta between the leading airflow and the tracking airflow. Likewise, the ACPH set point is decreased whenever the differential pressure error is less than a second percentage (e.g., 93%) of the maximum delta between the leading airflow and the tracking airflow, and the temperature is above the low temperature threshold and below the high temperature threshold. Other decision conditions can be used.

If the ACPH set point is to be increased, as determined in decision block 408, and the ACPH set point is not at a maximum value, as determined in decision block 410, the ACPH set point is increased in block 412. If, however, the ACPH set point is already at the maximum value, as determined in decision block 410, the ACPH set point is not changed in block 414. If, however, the ACPH set point is not to be increased, as determined in decision block 408, and the ACPH set point is to be decreased, as determined in decision block 416, and the ACPH set point is not at a minimum value, as determined in decision block 418, the ACPH set point is decreased in block 420. If, however, the ACPH set point is not to be decreased, as determined in decision block 416, the ACPH set point is not changed in block 414. If, however, the ACPH set point is already at the minimum value, as determined in decision block 418, the ACPH set point is not changed in block 414. After the ACPH set point is increased in block 412, or not changed in block 414, or decreased in block 420, one or more control signals are sent to the environmental control system in block 422 that maintain the differential pressure between the room and the one or more adjacent areas by adjusting: (a) the leading airflow to be approximately equal to the ACPH set point multiplied by a volume of the room divided by 60, and (b) the tracking airflow to maintain the volume differential set point.

Figure 5:
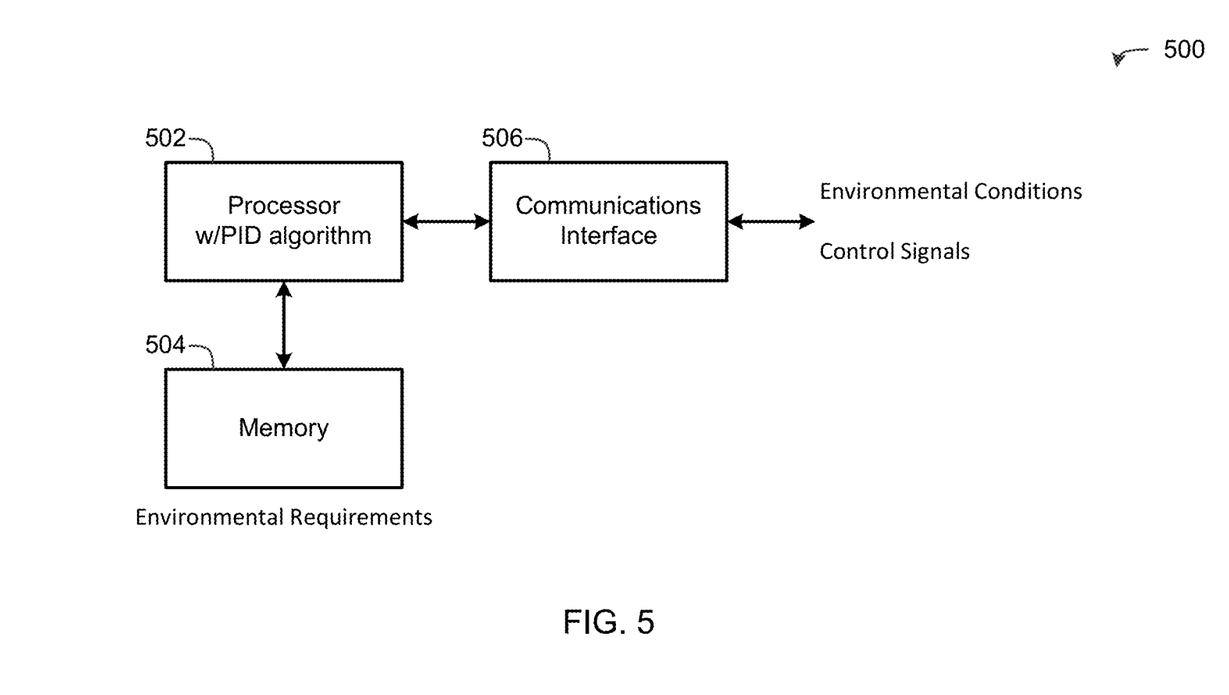
FIG. 5 is a block diagram of an apparatus for controlling an environmental control system to maintain a differential pressure between a room and one or more adjacent areas according to an embodiment of the current invention.

Referring now to FIG. 5, a block diagram of an apparatus 500 for controlling an environmental control system to maintain a differential pressure between a room and one or more adjacent areas according to an embodiment of the current invention is shown. The apparatus 500 includes a processor 502 with a PID algorithm, a memory 504 communicably coupled to the processor 502 and a communications interface 506 communicably coupled to the processor 502. Note that the apparatus 500 can be an existing environmental control system that is modified or retrofitted to perform the one or more of the methods described herein. The processor 502 communicably obtains the environmental requirements from the memory 504 and receives the environmental conditions via the communications interface 506. The processor 502 then performs one or more of the methods described herein and sends one or more signals to the environmental control systems via the communications interface 506 to maintain a differential pressure between a room and one or more adjacent areas.

To facilitate the understanding of this invention, a number of terms are defined below. Terms defined herein have meanings as commonly understood by a person of ordinary skill in the areas relevant to the present invention. Note that these terms may be used interchangeable without limiting the scope of the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm steps described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. Similarly, steps of a method or process described herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art.

All of the systems, devices, computer programs, compositions and/or methods disclosed and claimed herein can be made and executed without undue experimentation in light of the present disclosure. While the systems, devices, computer programs, compositions and methods of this invention have been described in terms of preferred embodiments, it will be apparent to those of skill in the art that variations may be applied to the systems, devices, computer programs, compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for controlling an environmental control system to maintain a differential pressure between a room and one or more adjacent areas, comprising the steps of:
    monitoring a temperature in the room, the differential pressure, a leading airflow for the room and a tracking airflow for the room;
    determining a differential pressure error based on the differential pressure and a differential pressure set point using a proportional-integral-derivative (PID) controller;
    increasing an air change per hour set point whenever: (a) the temperature exceeds a high temperature threshold, (b) the temperature falls below a low temperature threshold and the environmental control system is operating at approximately 100% of heating capacity, or (c) the differential pressure error is greater than a first percentage of a maximum delta between the leading airflow and the tracking airflow;
    decreasing the air change per hour set point whenever the differential pressure error is less than a second percentage of the maximum delta between the leading airflow and the tracking airflow, and the temperature is above the low temperature threshold and below the high temperature threshold; and
    sending one or more control signals to the environmental control system that maintain the differential pressure between the room and the one or more adjacent areas by adjusting: (a) the leading airflow to be approximately equal to the air flow change set point multiplied by a volume of the room divided by 60, and (b) the tracking airflow to maintain a volume differential set point.

2. The method of claim 1, further comprising the step of obtaining the volume of the room, the high temperature threshold, the low temperature threshold, the differential pressure set point, the air change per hour set point, the volume differential set point and the maximum delta between the leading airflow and the tracking airflow.

3. The method of claim 1, wherein:
the step of increasing the air change per hour set point is not performed if the increased air change per hour set point would exceed a maximum air change per hour set point; and
the step of decreasing the air change per hour set point is not performed if the decreased air change per hour set point would be below a minimum air change per hour set point.

4. The method of claim 3, further comprising the step of obtaining the minimum air change per hour set point and the maximum air change per hour set point.

5. The method of claim 3, wherein the maximum air change per hour comprises a first maximum air change per hour when the environmental control system is in a heating mode and a second maximum air change per hour when the environmental control system is in a cooling mode, wherein the first maximum air change per hour is less than the second maximum air change per hour.

6. The method of claim 5, further comprising the step of obtaining the first maximum air change per hour and the second maximum air change per hour.

7. The method as recited in claim 1, wherein:
the first percentage is approximately 97%; and
the second percentage is approximately 93%.

8. The method as recited in claim 1, further comprising the step of changing the high temperature threshold, the low temperature threshold, the differential pressure set point, the air change per hour set point, the volume differential set point, the maximum delta between the leading airflow and the tracking airflow, the first percentage or the second percentage.

9. The method of claim 1, further comprising:
monitoring a humidity in the room;
increasing the air change per hour set point whenever the humidity exceeds a high humidity threshold; and
wherein the step of decreasing the air change per hour set point comprise decreasing the air change per hour set point whenever the differential pressure error is less than a second percentage of the maximum delta between the leading airflow and the tracking airflow, and the temperature is above the low temperature threshold and below the high temperature, and the humidity is below the high humidity threshold.

10. The method of claim 9, further comprising the step of obtaining the high humidity threshold.

11. An apparatus for controlling an environmental control system to maintain a differential pressure between a room and one or more adjacent areas, comprising:
a communications interface;
a memory; and
a processor communicably coupled to the communications interface and the memory, wherein the processor (1) receives a temperature in the room, the differential pressure, a leading airflow for the room and a tracking airflow for the room via the communications interface, (2) determines a differential pressure error based on the differential pressure and a differential pressure set point using a proportional-integral-derivative (PID) algorithm, (3) increases an air change per hour set point whenever: (a) the temperature exceeds a high temperature threshold, (b) the temperature falls below a low temperature threshold and the environmental control system is operating at approximately 100% of heating capacity, or (c) the differential pressure error is greater than a first percentage of a maximum delta between the leading airflow and the tracking airflow, (4) decreases the air change per hour set point whenever the differential pressure error is less than a second percentage of the maximum delta between the leading airflow and the tracking airflow, and the temperature is above the low temperature threshold and below the high temperature threshold, and (5) sends one or more control signals to the environmental control system via the communications interface that maintain the differential pressure between the room and the one or more adjacent areas by adjusting: (a) the leading airflow to be approximately equal to the air flow change set point multiplied by a volume of the room divided by 60, and (b) the tracking airflow to maintain a volume differential set point.

12. The apparatus of claim 11, wherein the processor further obtains the volume of the room, the high temperature threshold, the low temperature threshold, the differential pressure set point, the air change per hour set point, the volume differential set point and the maximum delta between the leading airflow and the tracking airflow from the memory.

13. The apparatus of claim 11, wherein:
the processor does not increase the air change per hour set point when the increased air change per hour set point would exceed a maximum air change per hour set point; and
the processor does not decrease the air change per hour set point when the decreased air change per hour set point would be below a minimum air change per hour set point.

14. The apparatus of claim 13, wherein the processor further obtains the minimum air change per hour set point and the maximum air change per hour set point from the memory.

15. The apparatus of claim 13, wherein the maximum air change per hour comprises a first maximum air change per hour when the environmental control system is in a heating mode and a second maximum air change per hour when the environmental control system is in a cooling mode, wherein the first maximum air change per hour is less than the second maximum air change per hour.

16. The apparatus of claim 15, wherein the processor further obtains the first maximum air change per hour and the second maximum air change per hour from the memory.

17. The apparatus as recited in claim 11, wherein:
the first percentage is approximately 97%; and
the second percentage is approximately 93%.

18. The apparatus as recited in claim 11, wherein the processor further receives a change to the high temperature threshold, the low temperature threshold, the differential pressure set point, the air change per hour set point, the volume differential set point, the maximum delta between the leading airflow and the tracking airflow, the first percentage or the second percentage via the communications interface.

19. The apparatus of claim 11, wherein the processor further receives a humidity in the room via the communications interface, increases the air change per hour set point whenever the humidity exceeds a high humidity threshold, and decreases the air change per hour set point whenever the differential pressure error is less than a second percentage of the maximum delta between the leading airflow and the tracking airflow, and the temperature is above the low temperature threshold and below the high temperature, and the humidity is below the high humidity threshold.

20. The apparatus of claim 19, wherein the processor further obtains the high humidity threshold from the memory.

\* \* \* \* \*